US012642590B2

(12) United States Patent
Schoepp et al.

(10) Patent No.: US 12,642,590 B2
(45) Date of Patent: Jun. 2, 2026

(54) TECHNIQUE FOR DETERMINING A VISUALIZATION BASED ON AN ESTIMATED SURGEON POSE

(71) Applicant: Stryker European Operations Limited, Carrigtwohill (IE)

(72) Inventors: Hans Schoepp, Freiburg (DE); Florian Herrmann, Schwanau (DE)

(73) Assignee: Stryker European Operations Limited, Carrigtwohill (IE)

( * ) Notice: Subject to any disclaimer, the term of this patent is extended or adjusted under 35 U.S.C. 154(b) by 62 days.

(21) Appl. No.: 18/143,121

(22) Filed: May 4, 2023

(65) Prior Publication Data

US 2023/0355310 A1    Nov. 9, 2023

(30) Foreign Application Priority Data

May 6, 2022    (EP) ..................................... 22171974

(51) Int. Cl.
A61B 34/10        (2016.01)
A61B 34/20        (2016.01)
A61B 90/00        (2016.01)

(52) U.S. Cl.
CPC .............. A61B 34/10 (2016.02); A61B 34/20 (2016.02); A61B 90/361 (2016.02); A61B 90/37 (2016.02);
(Continued)

(58) Field of Classification Search
CPC ....... A61B 34/10; A61B 34/20; A61B 90/361; A61B 90/37; A61B 2034/105;
(Continued)

(56) References Cited

U.S. PATENT DOCUMENTS

| | | | |
|---|---|---|---|
| 7,050,845 B2 | 5/2006 | Vilsmeier | |
| 10,548,667 B2 | 2/2020 | Flett et al. | |

(Continued)

FOREIGN PATENT DOCUMENTS

| | | |
|---|---|---|
| DE | 102015102768 A1 | 9/2016 |
| DE | 102015102776 A1 | 9/2016 |

(Continued)

OTHER PUBLICATIONS

Andersen, Daniel et al., "A Hand-Held Self-Contained Simulated Transparent Display", IEEE International Symposium on Mixed and Augmented Reality (Ismar-Adjunct), Sep. 19, 2016, pp. 96-101.

(Continued)

*Primary Examiner* — Pascal M Bui Pho
*Assistant Examiner* — Nicholas A Robinson
(74) *Attorney, Agent, or Firm* — Howard & Howard Attorneys PLLC

(57)        ABSTRACT

A method, a system, and a computer program for determining a visualization of content to be displayed to a surgeon on a display of a portable display device are provided. First pose data indicative a first pose of an anatomical feature of a patient in an operating room and second pose data indicative of a second pose of a portable display device in the operating room are obtained. Based on the first pose data and the second pose data, a third pose of a surgeon relative to the patient is estimated. Based on the estimated third pose, a visualization of content to be displayed to the surgeon on a display of the portable display device is determined.

19 Claims, 4 Drawing Sheets

(52) U.S. Cl.
CPC ... *A61B 2034/105* (2016.02); *A61B 2034/107* (2016.02); *A61B 2034/2057* (2016.02); *A61B 2034/2065* (2016.02); *A61B 2090/372* (2016.02)

(58) Field of Classification Search
CPC ...... A61B 2034/107; A61B 2034/2057; A61B 2034/2065; A61B 2090/372; A61B 2017/00207; A61B 2034/2055; A61B 2090/368; A61B 2090/3983; A61B 34/30; G06F 3/011; G06F 3/04845; G06F 3/1454; G06T 7/70; G06T 19/003; G06T 2207/10121; G16H 30/20
See application file for complete search history.

(56) References Cited

U.S. PATENT DOCUMENTS

| | | | |
|---|---|---|---|
| 10,702,343 B2 | 7/2020 | Kozak et al. | |
| 10,786,287 B2 | 9/2020 | Beger et al. | |
| 10,980,578 B2 | 4/2021 | Beger et al. | |
| 2003/0129567 A1* | 7/2003 | Cabato | F41H 5/266 |
| | | | 434/38 |
| 2014/0275940 A1* | 9/2014 | Hladio | A61B 90/70 |
| | | | 600/407 |
| 2016/0128783 A1* | 5/2016 | Hladio | A61B 34/10 |
| | | | 600/424 |
| 2019/0159860 A1* | 5/2019 | Teranuma | A61B 1/05 |
| 2019/0183321 A1* | 6/2019 | Teranuma | H04N 23/555 |
| 2021/0259789 A1* | 8/2021 | Wright | A61B 34/35 |
| 2021/0378750 A1 | 12/2021 | Navab et al. | |
| 2023/0022929 A1* | 1/2023 | Wright | G06V 40/18 |

FOREIGN PATENT DOCUMENTS

| | | | |
|---|---|---|---|
| DE | 102016115605 A1 | 3/2018 | |
| EP | 1321105 B1 | 8/2003 | |
| EP | 1470791 B1 | 2/2007 | |
| EP | 3081184 B1 | 1/2019 | |
| EP | 3692939 A1 | 8/2020 | |
| EP | 3858280 A1 | 8/2021 | |
| WO | 9832388 A2 | 7/1998 | |
| WO | 2018049196 A1 | 3/2018 | |
| WO | 2019141704 A1 | 7/2019 | |

OTHER PUBLICATIONS

Andersen, Daniel et al., "Augmented Visual Instruction for Surgical Practice and Training", IEEE Workshop on Augmented and Virtual Realities for Good (Var4Good), Mar. 18, 2018, pp. 1-5.
Wen, Rong et al., "Augmented Reality Guidance with Multimodality Imaging Data and Depth-Perceived Interaction for Robot-Assisted Surgery", Robotics, vol. 6, No. 2, May 24, 2017, p. 13.
English language abstract for EP 1 321 105 B1 extracted from espacenet.com database on May 6, 2023, 2 pages.
English language abstract and machine-assisted English translation for EP 1 470 791 B1 extracted from espacenet.com database on May 6, 2023, 13 pages.
Machine-assisted English language abstract for DE 10 2015 102 768 A1 extracted from espacenet.com database on May 6, 2023, 3 pages.
English language abstract for DE 10 2016 115 605 A1 extracted from espacenet.com database on May 6, 2023, 1 page.
Machine-assisted English language abstract for DE 10 2015 102 776 A1 extracted from espacenet.com database on May 6, 2023, 4 pages.

* cited by examiner

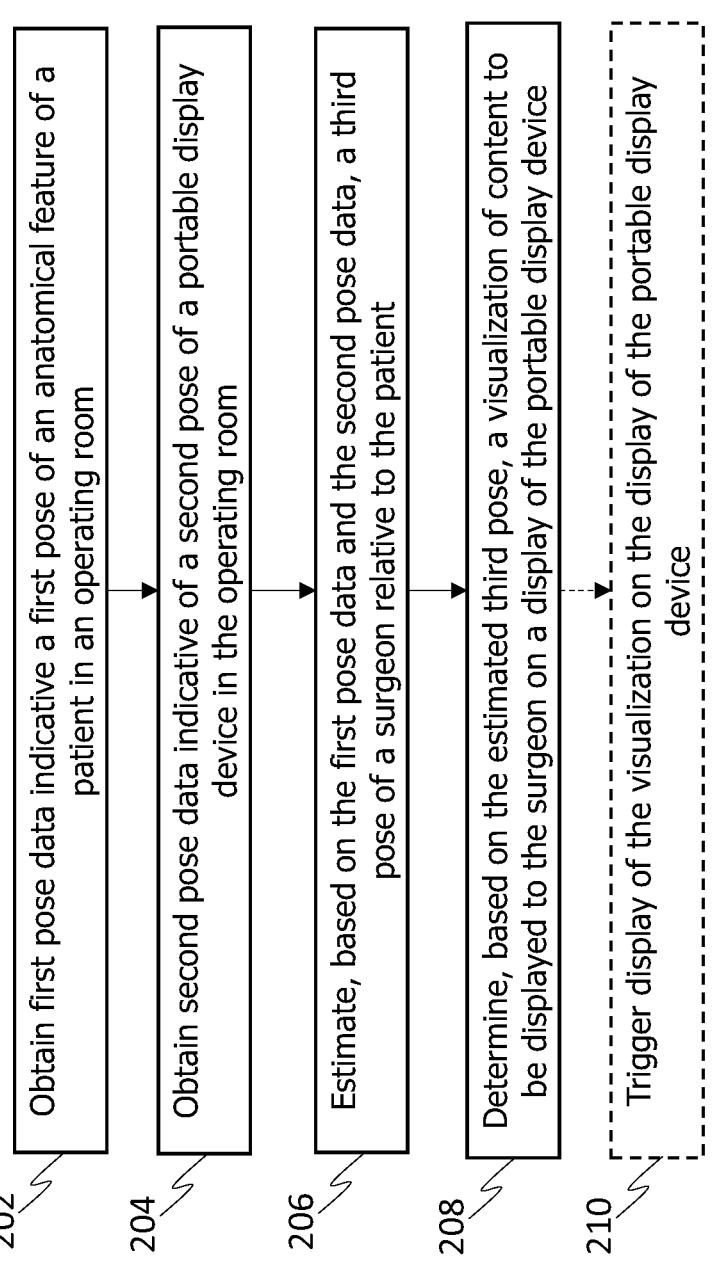

202 — Obtain first pose data indicative a first pose of an anatomical feature of a patient in an operating room 204 — Obtain second pose data indicative of a second pose of a portable display device in the operating room 206 — Estimate, based on the first pose data and the second pose data, a third pose of a surgeon relative to the patient 208 — Determine, based on the estimated third pose, a visualization of content to be displayed to the surgeon on a display of the portable display device 210 — Trigger display of the visualization on the display of the portable display device

Fig. 2

TECHNIQUE FOR DETERMINING A VISUALIZATION BASED ON AN ESTIMATED SURGEON POSE

PRIORITY CLAIM

This application claims priority under 35 U.S.C. § 119 to European Patent Application No. 22171974.3, filed May 6, 2022, the entire contents of which are hereby incorporated by reference.

TECHNICAL FIELD

The present disclosure generally relates to a technique for determining a visualization of content to be displayed to a surgeon on a display of a portable display device. The present disclosure also relates to an associated system and computer program.

BACKGROUND

In recent years, computer-assisted surgery (CAS) and robot-assisted surgery (RAS) have been established in the clinical field. In CAS and RAS, a surgeon may be provided with a visualization that informs the surgeon about a pose of an anatomical element of a patient's body, for example relative to a navigated surgical instrument moved by the surgeon or a tool held by a surgical robot. Other information such as pre-planned objects (e.g., trajectories, implants or tissue to be resected) may also be visualized.

Such visualizations may be provided to the surgeon via a display mounted on a cart of a surgical navigation system. In this case, the display must be positioned up to several meters away from the patient to enable the surgeon to access the patient for performing a surgical procedure. Due to this arrangement, the surgeon may need to swap his field of view from the surgical field on the patient to the display on the cart of the surgical navigation system and back. Swapping the field of view may involve eye and head movement of the surgeon and will add cognitive load on the surgeon, because the surgeon may need to transform the visualization provided on the display by mentally adapting the orientation of visualized content to comply with his view of the surgical field. The surgeon may need to adjust the focus of his eyes every time he or she changes the field of view between the surgical field and the display mounted on the cart of the surgical navigation system, thereby causing distractions and fatigue.

SUMMARY

There is a need for a technique that solves one or more of the aforementioned or other problems.

According to a first aspect, a method for determining a visualization of content to be displayed to a surgeon on a display of a portable display device is provided. The method comprises obtaining first pose data indicative a first pose of (e.g., an anatomical feature of) a patient in an operating room, and obtaining second pose data indicative of a second pose of a portable display device in the operating room. The method further comprises estimating, based on the first pose data and the second pose data, a third pose of a surgeon relative to (e.g., the anatomical feature of) the patient. The method comprises determining, based on the estimated third pose, a visualization of content to be displayed to the surgeon on a display of the portable display device.

The method may be performed by at least one processor. The method may be a computer-implemented method. The method does not comprise a step requiring a substantial interaction with a human or animal body. The method does not comprise a surgical step.

In accordance with the present disclosure, a "pose" may comprise at least one of a position and an orientation.

The third pose may be estimated without tracking the surgeon (e.g., by a surgical tracking system). The surgeon may not need to be provided with one or more trackers (e.g., trackable by the surgical tracking system).

The portable display device may be configured such that the surgeon can recognize the displayed content from a distance (e.g., larger than 10 cm, 20 cm, 50 cm or 70 cm). The surgeon may not need to wear the portable display device (e.g., as a HMD). The portable display device may be placed close to (e.g., less than 1 m away from) a surgical field. The portable display device may be configured to be placed on the patient's body (e.g., while displaying the content to the surgeon). The portable display device may fulfil at least one of the following conditions: (i) it is a wireless device; (ii) it is a non-wearable device; (iii) it is movable relative to the surgeon; (iv) it is remote from the surgeon (e.g., >20 cm distant from an eye of the surgeon); (v) it is separate from (e.g., a cart of) a surgical tracking system; (vi) it is or comprises a tablet computer; (vii) the display or the complete portable display device is configured to be covered by a surgical drape (e.g., while displaying the content to the surgeon); (viii) the portable display device comprises a user interface for entering user input. The portable display device may not be a HMD. The display may be a non-transparent or non-see-through display. A backside of the display may be opaque. The display may be a touch screen.

The method may comprise obtaining a fourth pose of the surgeon relative to the portable display device. The third pose may be estimated further based on the fourth pose.

The fourth pose may be determined based on a predefined spatial criterion associated with the portable display device. The predefined spatial criterion may define that the fourth pose lies on a trajectory having a predefined spatial relationship relative to the portable display device. The trajectory may be parallel to a normal of the display of the portable display device. The trajectory may intersect (e.g., a center of) the display of the portable display device.

Alternatively or additionally, the fourth pose may be determined based on sensor data acquired by a sensor of the portable display device. The sensor data may be indicative of a spatial relationship between the surgeon and the portable display device.

An approximate fourth pose may be determined based on the predefined spatial criterion. The approximate fourth pose may be refined based on the sensor data to determine the fourth pose.

The sensor may comprise a camera. The sensor data may comprise image data acquired by the camera. The image data may comprise an image of at least a part of the surgeon.

The sensor may comprise a depth sensor. The sensor data may comprise depth data acquired by the depth sensor. The depth data may be representative of a distance between the depth sensor and at least a part of the surgeon.

At least one of the first pose data and the second pose data may be obtained from a (e.g., the) surgical tracking system. The first pose data may be obtained from the surgical tracking system that is configured to track the anatomical feature or one or more trackers fixedly attached relative to the anatomical feature. Alternatively or additionally, the second pose data may be obtained from the surgical tracking system that is configured to track the portable display device or one or more trackers fixedly attached relative to the portable display device. The surgical tracking system may be an optical tracking system. The surgical tracking system may be configured to track at least one entity selected from the anatomical feature, the portable display device and the one or more trackers by acquiring image data comprising at least one image of the at least one entity. The image data may be acquired by one or more image sensors of the surgical tracking system that are configured to detect at least one of infrared light and visual light. A tracker in accordance with the present disclosure may comprise one or more active or passive tracking markers detectable by the surgical tracking system.

The visualization may be determined based on a viewing direction of the surgeon onto (e.g., the anatomical feature of) the patient. The viewing direction may be determined based on the fourth pose. The viewing direction may be determined as a direction from the surgeon towards (e.g., the anatomical feature of) the patient. The viewing direction may be determined further based on the sensor data. For example, the viewing direction may be determined based on an orientation of the surgeon's head relative to the portable display device, the orientation being detected based on the sensor data.

The content may be associated with the anatomical feature. The content may be associated with one or more anatomical features of the patient having a predefined spatial relationship to the viewing direction. The one or more anatomical features may comprise the anatomical feature having the first pose. An "anatomical feature" according to the present disclosure may comprise at least one of (i) an anatomical element such as a bone, an organ or the like, and (ii) a shape of at least portion of a surface of the patient's body.

The visualization may be an augmented view of (i) the content and (ii) the anatomical feature or a representation of the anatomical feature. The visualization may be an augmented view of (i) the content and (ii) the one or more anatomical features or a representation thereof (i.e., a representation of the one or more anatomical features).

The visualization may mimic the view of the surgeon onto (e.g., the anatomical feature of) the patient. The visualization may correspond to a view of the surgeon onto (e.g., the anatomical feature of) the patient and comprise the content overlaid onto the view. The (e.g., one or more) anatomical feature(s) or the representation thereof may be displayed in an orientation relative to the surgeon that corresponds to the orientation of the corresponding anatomical feature(s) of the patient relative to the surgeon. The visualization may be determined such that (e.g., an orientation of) the displayed content complies or corresponds to with a viewing direction of the surgeon onto (e.g., the anatomical feature of) the patient.

The visualization may be determined further based on the obtained second pose. The visualization may be determined based on a line of sight of the surgeon onto the display of the portable display device. The visualization may be determined such that a projection of the visualization along the line of sight complies with a view along the viewing direction of the surgeon onto (e.g., the anatomical feature of) the patient.

The method may further comprise triggering display of the visualization on the display of the portable display device.

The display and the camera of the portable display device may face in a similar direction. The camera of the portable display device may be a camera configured to acquire an image of a person looking at the display of the portable display device (e.g., an image of the surgeon).

The method may further comprise comparing at least one pose selected from the second pose, the third pose and the fourth pose with a predefined criterion. The method may comprise, based on a result of the comparing, performing one or more predefined actions associated with the result. The predefined criterion may define a preset maximum deviation from a previously obtained instance of the at least one pose. If (e.g., only if) the result of the comparing is indicative of the at least one pose exceeding the preset maximum deviation, the visualization may be at least one of (i) determined and (ii) triggered to be displayed on the display of the portable display device.

The method may further comprise obtaining user input entered via the portable display device. The method may comprise performing one or more actions based on the obtained user input. The user input may comprise a gesture command entered via the sensor.

In a first variant, the method may not comprise the step of determining, based on the estimated third pose, a visualization of content to be displayed to the surgeon on a display of the portable display device. In the first variant, the method may comprise performing one or more predefined actions associated with the estimated third pose. In the first variant, the one or more predefined actions may comprise at least one of the following: (i) triggering display of information determined based on the estimated third pose; (ii) triggering display of an indication of the estimated third pose; (iii) forwarding information indicative of the estimated third pose to the portable display device; (iv) determining, based on the estimated third pose, a visualization of content to be displayed to the surgeon on a display of the portable display device.

In a second variant, the method may not comprise one or more of (i) the step of obtaining first pose data indicative a first pose of an anatomical feature of a patient in an operating room, (ii) the step of estimating, based on the first pose data and the second pose data, a third pose of a surgeon relative to the patient, and (iii) the step of determining, based on the estimated third pose, a visualization of content to be displayed to the surgeon on a display of the portable display device. In the second variant, the method may comprise, after having obtained the second pose data, estimating, based on the first pose data, a fourth pose of the surgeon in the operating room. In the second variant, the step of estimating the fourth pose may comprise at least one of (i) obtaining the fourth pose as described herein and (i) determining the fourth pose as described herein. In the second variant, the method may comprise performing one or more predefined actions associated with the estimated fourth pose. In the second variant, the one or more predefined actions may comprise at least one of the following: (i) triggering display of information determined based on the estimated fourth pose; (ii) triggering display of an indication of the estimated fourth pose; (iii) forwarding information indicative of the estimated fourth pose to the portable display device; (iv) determining, based on the estimated fourth pose, a visualization of content to be displayed to the surgeon on a display of the portable display device.

According to a second aspect, a system for determining a visualization of content to be displayed to a surgeon on a display of a portable display device is provided. The system comprises at least one processor configured to obtain first pose data indicative a first pose of (e.g., an anatomical feature of) a patient in an operating room, and obtain second pose data indicative of a second pose of a portable display device in the operating room. The at least one processor is configured to estimate, based on the first pose data and the second pose data, a third pose of a surgeon relative to (e.g., the anatomical feature of) the patient. The at least one processor is further configured to determine, based on the estimated third pose, a visualization of content to be displayed to the surgeon on a display of the portable display device.

The at least one processor may be configured to perform the method according to the first aspect.

The system may further comprise the portable display device. The portable display device may be configured as described above for the first aspect.

The system may further comprise a surgical tracking system. The surgical tracking system may be configured as described above for the first aspect. The surgical tracking system may be configured to track at least one entity selected from (i) the anatomical feature, (ii) one or more trackers fixedly attached relative to the anatomical feature, (iii) the portable display device, and (iv) one or more trackers fixedly attached relative to the portable display device. The surgical tracking system may be configured to provide the at least one processor with at least one input selected from the first pose data and the second pose data. The at least one processor may be configured to obtain the at least one input from the surgical tracking system.

According to a third aspect, a computer program is provided. The computer program comprises instructions which, when executed on at least one processor, cause the at least one processor to carry out or perform the method according to the first aspect. Also provided is a computer program product comprising instructions which, when executed on at least one processor, cause the at least one processor to carry out or perform the method according to the first aspect. The computer program may be stored on one or more (e.g., non-transitory) computer readable media or carried by a data stream. The present disclosure also provides for such computer readable media and such a data stream.

BRIEF DESCRIPTION OF THE DRAWINGS

Further details, advantages and aspects of the present disclosure will become apparent from the following embodiments taken in conjunction with the drawings, wherein:

FIG. 2 shows a method in accordance with the present disclosure;

DETAILED DESCRIPTION

Figure 1:
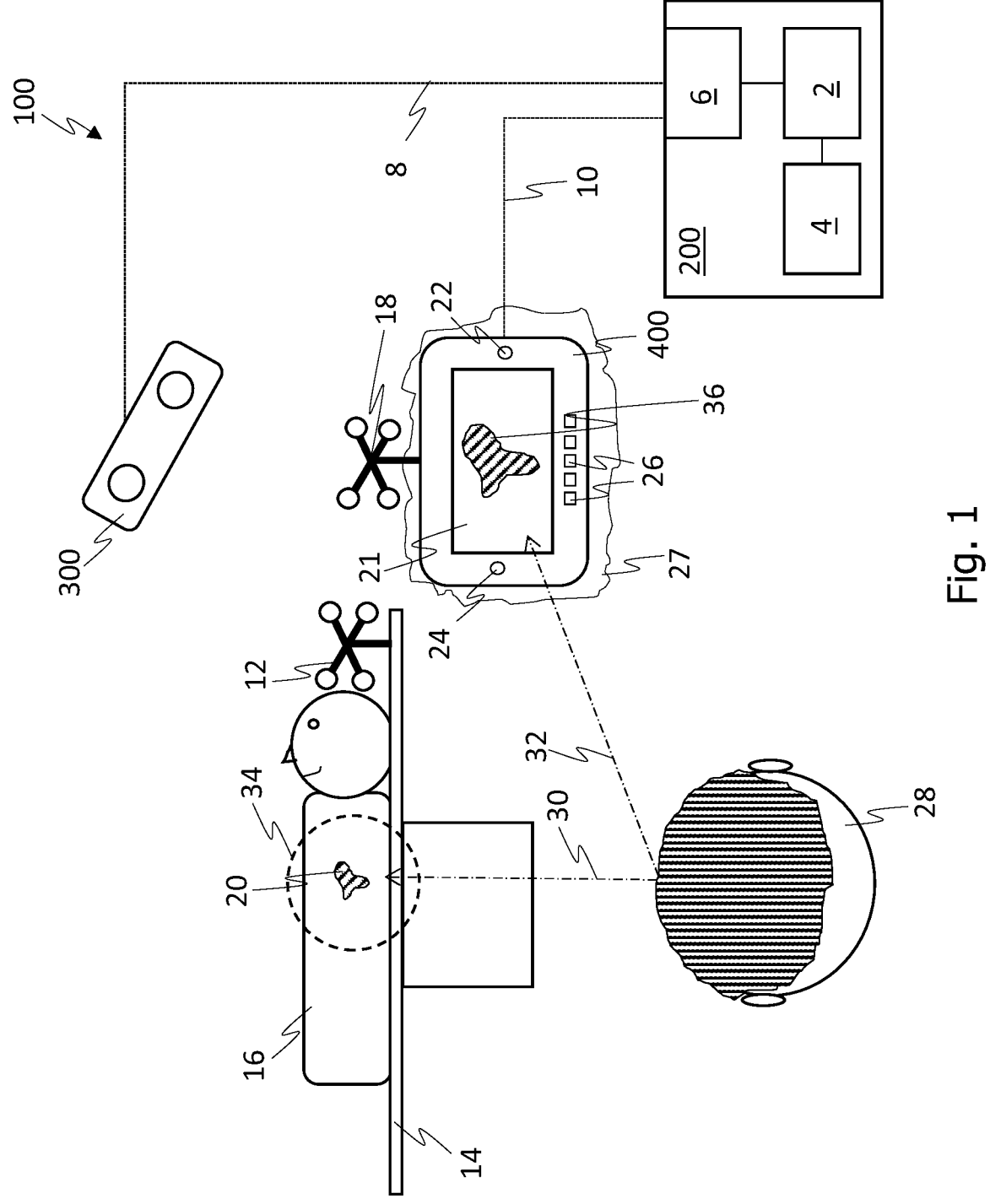
FIG. 1 shows a system in accordance with the present disclosure.

In the following description, exemplary embodiments of a system and a method will be explained with reference to the drawings. The same reference numerals will be used to denote the same or similar structural features.

FIG. 1 shows a system 100 in accordance with the present disclosure. The system 100 comprises a computing system 200. The computing system 200 comprises a processor 2 coupled to a memory 4 and an interface 6. The system 100 further comprises a surgical tracking system 300 connected to the interface 6 via a wired or wireless communication connection 8, and a portable display device 400 connected to the interface 6 via a wired or wireless communication connection 10. Other variants of connecting the processor 2 with the surgical tracking system 300 and the portable display device 400 (e.g., using a plurality of interfaces or relay devices) are also possible.

The surgical tracking system 300 is an optical tracking system configured to track a first tracker 12 fixed to a patient support 14 holding a patient 16. The first tracker 12 has a fixed spatial relationship to the anatomical feature 20 of the patient 16. The surgical tracking system 300 is further configured to track a second tracker 18 that is attached to the portable display device 400.

In one variation, the surgical tracking system 300 may be configured to track (e.g., the anatomical feature 20 of) the patient 16 directly, instead of tracking the first tracker 12. Alternatively or additionally, the surgical tracking system 300 may be configured to track the portable display device 400 directly, instead of tracking the second tracker 18. In these cases, one or both of the respective trackers 12, 18 may be omitted. For tracking (e.g., anatomical feature 20 of) the patient 16 and the portable display device 400 directly, the surgical tracking system 300 may comprise one or more image sensors configured to acquire an image using visible light. The (e.g., anatomical feature 20 of the) patient 16 and the portable display device 400 may then be detected in the image using appropriate image analysis techniques (e.g., object recognition). Other variants for directly tracking (e.g., the anatomical feature 20 of) the patient 16 and the portable display device 400 are also possible (e.g., using a time-of-flight sensor, a thermal camera or the like).

The portable display device 400 is a tablet computer and comprises a display 21 that is configured as a touch screen. The portable display device 400 further comprises a frontal selfie camera 22 facing a person looking at the display 21. Alternatively or in addition to the camera 22, the portable display device 400 comprises a depth sensor 24 configured to measure a distance between the portable display device 400 and the person looking at the display 21. The portable display device 400 may further comprise various buttons 26 as part of a user interface. The portable display device 400 is configured to display, on the display 21, content to a surgeon 28. The portable display device 400 may be configured to be sterilized. Alternatively or additionally, the portable display device 400 may be configured to display the content 36 to the surgeon 28 while being covered by a surgical drape 27. In FIG. 1, the head of the surgeon 28 is illustrated from behind to indicate that the surgeon is looking toward the patient 16 along the viewing direction 30 or onto the display 21 along the line of sight 32.

The portable display device 400 may be placed in close proximity to (e.g., <1 m, <50 cm or even <30 cm away from) the surgical field 34. This may minimize the amount of head and eye movement required by the surgeon to change his field of view from the surgical field 34 to the display 21 and back. Furthermore, the surgeon 28 does not need to wear a HMD to be provided with the visualization. Instead, the surgeon 28 may simply look at the portable display device 400 whenever (s)he intends to do so.

FIG. 2 shows a method in accordance with the present disclosure. The method may be performed by the processor 2. The memory 4 may store instructions which, when executed by the processor 2, cause the processor 2 to perform the method described herein.

In step 202, first pose data indicative of a first pose of the anatomical feature 20 of the patient 16 in the operating room is obtained. The first pose data may alternatively or additionally be indicative of a first pose of the patient 16 in the operating room. The first pose data is obtained from the surgical tracking system 300 and is indicative of a position and orientation of (e.g., the anatomical feature 20 of) the patient 16 relative to the surgical tracking system 300. The first pose data may be determined by tracking, with the surgical tracking system 300, the first tracker 12 or by directly tracking (e.g., the anatomical feature 20 of) the patient 16 with the surgical tracking system 300.

In step 204, second pose data indicative of a second pose of the portable display device 400 in the operating room is obtained. The second pose data is obtained from the surgical tracking system 300 and is indicative of a position and orientation of the portable display device 400 relative to the surgical tracking system 300. The second pose data may be determined by tracking, with the surgical tracking system 300, the second tracker 18 or by directly tracking the portable display device 400 with the surgical tracking system 300. In a still further variant, the second pose data may be obtained from the portable display device 400 configured to determine its position and orientation in the operating room using one or more of its sensor(s) (e.g., the camera 22 and/or the depth sensor 24).

In step 206, (e.g., only) based on the first pose data and the second pose data, a third pose of the surgeon 28 relative to (e.g., the anatomical feature 20 of) the patient 16 is estimated.

Due to the estimation of the third pose based on the first pose data and the second pose data, the surgeon 28 does not need to be tracked by the surgical tracking system 300. In other words, the only data obtained from the surgical tracking system 300 for determining the third pose may be the first pose data and the second pose data. There is no need to attach an additional tracker to the surgeon 28 to obtain the third pose of the surgeon 28.

The method may comprise obtaining a fourth pose of the surgeon 28 relative to the portable display device 400. The third pose of the surgeon 28 relative to the patient 16 may then be estimated further based on the fourth pose.

Based on the fourth pose and the second pose, a position and orientation of the surgeon 28 relative to the surgical tracking system 300 can be determined. The first pose is indicative of a position and orientation of (e.g., the anatomical feature 20 of) the patient 16 in the operating room. Thus, the position and orientation of (e.g., the anatomical feature 20 of) the patient 16 and the position and orientation of the surgeon 28 are each known relative to the surgical tracking system 300. Based on these positions and orientations, the fourth pose of the surgeon relative to the portable display device 400 can be determined.

An approximate fourth pose, also referred to as roughly estimated fourth pose, may be determined to lie on a trajectory having a predefined spatial relationship relative to the portable display device 400. The trajectory is parallel to a normal of the display of the portable display device and intersects a center of the display of the portable display device. In other words, it may be assumed that the surgeon 28 positions the display 21 such that it faces towards him.

In some cases, the fourth pose of the surgeon 28 lies exactly on the trajectory. In these cases, the roughly estimated fourth pose may be taken as the fourth pose. Otherwise, the roughly estimated fourth pose may be refined based on sensor data acquired by the camera 22 or the depth sensor 24 of the portable display device 400, thereby determining the fourth pose. For instance, a precise location of the surgeon 28 may be determined in an image acquired by the camera 22. The approximate fourth pose may be used for detecting the precise location of the surgeon 28 in the image, for example by detecting a human face that is closest to the trajectory.

In step 208, based on the estimated third pose, a visualization of content to be displayed to the surgeon 28 on the display 21 of the portable display device 400 is determined.

The visualization may be determined based on the viewing direction 30 of the surgeon 28 onto the patient 16. The viewing direction 30 is determined as a direction from the surgeon 28 towards (e.g., the anatomical feature 20 of) the patient 16. The viewing direction 30 may be determined based on an orientation of the surgeon's head relative to the portable display device 400, the orientation being detected in an image acquired by the camera 22.

The content to be displayed to the surgeon 28 may include pre-planned objects such as implants, planned trajectories or body portions of interest. The content to be displayed is associated with one or more anatomical features of the patient 16, including the anatomical feature 20, which may have a predefined spatial relationship to the viewing direction 30. The content may include a model, segmentation or representation of the associated anatomical feature(s) of the patient 16. For example, content associated with all anatomical features that are intersected by the viewing direction 30 or that lie within a predefined distance around the viewing direction 30 may be displayed. The surgeon 28 may adapt the contents to be displayed.

The visualization may be an augmented view. The content may be overlaid onto the patient 16 or on an image thereof. The augmented view may comprise the content and the associated anatomical features or a representation (e.g., an image, model or segmentation) thereof.

The visualization to be displayed mimics the view of the surgeon 28 onto the patient 16, in particular a view of the surgeon 28 onto the surgical field 34 including the anatomical feature 20. The visualization may thus correspond to a view of the surgeon 28 onto the patient 16 and comprise the content overlaid onto the view. In other words, the visualization is determined such that the displayed (e.g., representation of the) anatomical feature(s) and the content associated therewith comply with the viewing direction 30 of surgeon 28 onto the patient 16.

The surgeon 28 may thus not need to transpose (e.g., rotate) the displayed content mentally when changing his field of view from the surgical field 34 to the display 21 and vice versa.

The visualization may be determined further based on the line of sight 32 of the surgeon 28 onto the display 21 of the portable display device 400. The visualization may be determined such that a projection of the visualization along the line of sight 32 complies with a view along the viewing direction 30 of the surgeon 28. Thereby, a potential distortion of the displayed content perceived by the surgeon 28 due to a sharp viewing angle onto the display 21 may be compensated.

In step 210, display of the visualization is triggered on the display 21 of the portable display device 400. The processor 2 may send a control command to the portable display device 400 to trigger display of the visualization. The processor 2 may send information (e.g., image data) representing or defining the visualization to be displayed to the portable display device 400.

In one example, only if the second pose, the third pose and/or the fourth pose exceed a preset maximum deviation from a previously obtained instance of the respective second, third or fourth pose, the visualization is determined and triggered to be displayed. This may avoid determining and updating the displayed visualization too often, thereby lowering processing time and reducing disturbance for the surgeon 28.

The method may further comprise obtaining user input entered via the portable display device 400. One or more predefined actions may be performed corresponding to the user input. For example, a navigation workflow may be started or the visualization may be adapted based on the user input. The user input may comprise a gesture command recognized based on image data acquired by the camera 22 or based on depth data acquired by the depth sensor 24. The user input may be entered via the touch screen 21 or the button(s) 26.

Figure 3B:
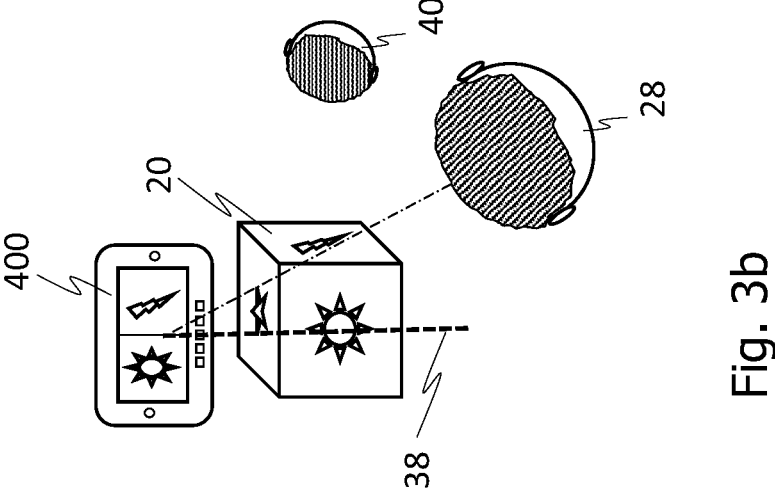
FIG. 3a-3b show exemplary visualizations in accordance with the present disclosure.
Figure 3A:
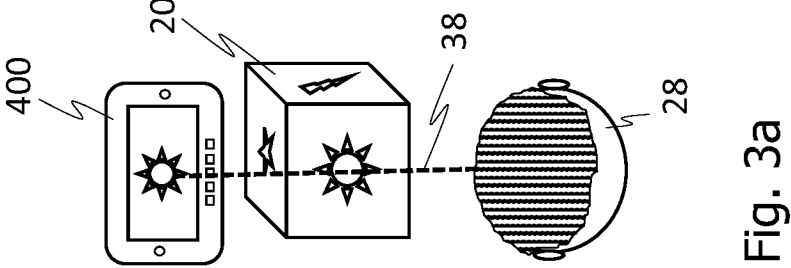

FIGS. 3a and 3b show exemplary visualizations in accordance with the present disclosure. In these figures, the anatomical feature 20 is schematically illustrated as a cube having distinguishable sides.

As illustrated in FIG. 3a, the surgeon 28 may be positioned on a trajectory 38 parallel to a normal of the display 21, the trajectory 38 originating at the middle of the display 21. The fourth pose of the surgeon 28 relative to the portable display device 400 can thus be determined by assuming that the surgeon 28 is positioned on the trajectory 38. The pose of the portable display device 400 and the pose of the anatomical feature 20 are obtained (e.g., in steps 202 and 204). A spatial relationship between the portable display device 400 and the anatomical feature 20 can be derived from these obtained poses. This allows estimating the pose of the surgeon 28 relative to the anatomical feature 20 (e.g., in step 206) based on the obtained first and second pose and based on the fourth pose. The visualization may then be determined (e.g., in step 208) such that it complies with a viewing direction of the surgeon 28 onto the anatomical feature 20. In the illustrated example, the determined visualization is displayed on the display 21 such that the surgeon 28 is presented with a view of a side of the anatomical feature 20 that is in his field of view.

As illustrated in FIG. 3b, the surgeon 28 may not be positioned on the trajectory 38. An approximate fourth pose of the surgeon 28 relative to the portable display device 400 may be determined by assuming that the surgeon 28 is located on the trajectory 38. This may be advantageous in case a plurality of persons are located in proximity of the portable display device 400. In the illustrated example, a nurse 40 is located in the operating room and may view the display 21. Nevertheless, the nurse 40 in this example is located further from the normal 38 than the surgeon 28. In other words, the display 21 is more suitably oriented for the surgeon 28 than for the nurse 40. The approximate fourth pose is thus closer to the real pose of the surgeon 28 than to that of the nurse 40.

To refine the approximate fourth pose of the surgeon 28, sensor data of the portable display device 400 may be obtained. For example, an image acquired by the camera 22 or depth data acquired by the depth sensor 24 may be used to detect a human (e.g., a human face). The surgeon 28 may be identified using facial recognition or object recognition (e.g., recognition of an identification patch worn by the surgeon or of clothing worn by the surgeon). A detected person located closest to the trajectory 38 may be assumed to be the surgeon 28, and its detected pose may be taken as the pose of the surgeon 28 relative to the portable display device 400. The approximate fourth pose may be refined by starting the facial recognition or the object recognition in an area of the image that is closest to the trajectory 38. Alternatively, the detected position of the surgeon 28 may be directly used as the fourth pose of the surgeon 28 without considering the approximate fourth pose or the trajectory 38.

Again, the pose of the anatomical feature 20 and the pose of the portable display device 400 are obtained (e.g., in steps 202 and 204), such that their relative positions and orientations are known. Based on the (e.g., refined) fourth pose of the surgeon 28 relative to the portable display device 400, the third pose of the surgeon 28 relative to the anatomical feature 20 is determined (e.g., in step 206). In the illustrated example, the surgeon 28 is presented with a view of two sides of the anatomical feature 20 that are in his field of view. If the approximate fourth pose were used instead of the refined fourth pose, the surgeon 28 would instead be presented with a view of a single side of the anatomical element 20 as illustrated in FIG. 3a.

Figure 4:
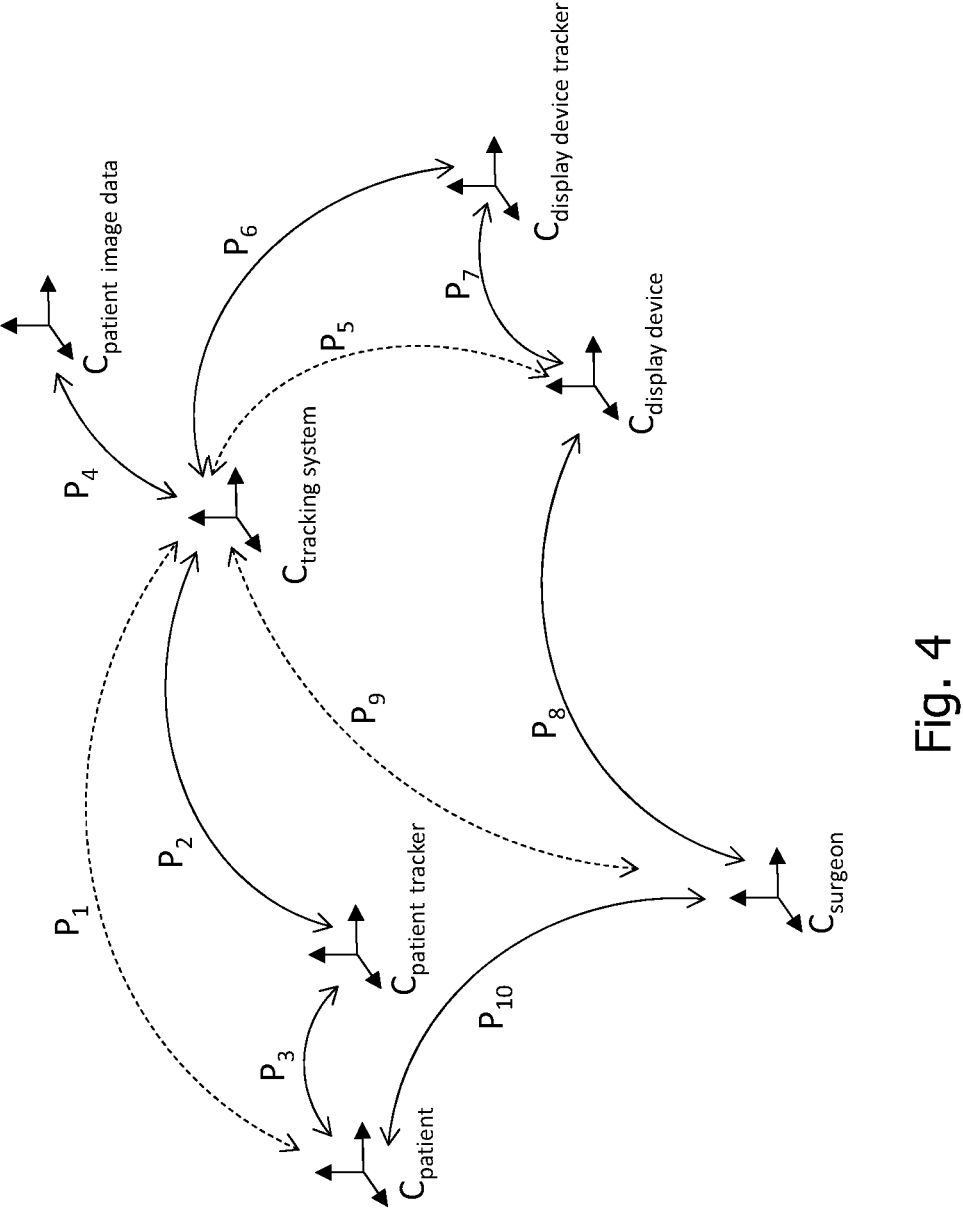
FIG. 4 shows exemplary coordinate systems of a system in accordance with the present disclosure.

FIG. 4 shows exemplary coordinate systems in accordance with the present disclosure.

The first pose of (e.g., the anatomical feature 20 of) the patient 16 may be obtained as pose $P_1$ in a coordinate system $C_{tracking\ system}$ of the surgical tracking system 300. The first pose may be determined based on a tracked pose $P_2$ of the first tracker 12 in the coordinate system $C_{tracking\ system}$ and based on a known relative pose $P_3$ between (e.g., the anatomical feature 20 of) the patient 16 and the first tracker 12. Alternatively, the first pose $P_1$ may be obtained by directly tracking (e.g., the anatomical feature 20 of) the patient 16 by the surgical tracking system 300 in the coordinate system $C_{tracking\ system}$.

The second pose of the portable display device 400 may be obtained as the pose $P_5$ in the coordinate system $C_{tracking\ system}$ of the surgical tracking system 300. The second pose may be determined based on a tracked pose $P_6$ of the second tracker 18 in the coordinate system $C_{tracking\ system}$ and based on a known relative pose $P_7$ between the portable display device 400 and second tracker 18. Alternatively, the second pose $P_5$ may be determined by directly tracking the portable display device 400 by the surgical tracking system 300 in the coordinate system $C_{tracking\ system}$.

The fourth pose $P_8$ of the surgeon 28 relative to the portable display device 400 may be obtained as described above. This may involve determining the approximate fourth pose and refining the approximate fourth pose based on the sensor data.

The poses $P_5$ and $P_8$, or of the poses $P_6$, $P_7$ and $P_8$ may be combined to obtain the pose $P_9$ of the surgeon 28 in the coordinate system $C_{tracking\ system}$. The third pose $P_{10}$ between the surgeon 28 and (e.g., the anatomical feature 20 of) the patient 16 may be determined based on the poses $P_1$ and $P_9$, or based on the poses $P_2$, $P_3$ and $P_9$. Instead of the pose $P_9$, a combination of the poses $P_5$ and $P_8$, or of the poses $P_6$, $P_7$ and $P_8$ may be used.

Using the approach described herein, no tracking of the surgeon 28 by the surgical tracking system 300 is required. Instead, the pose $P_9$ is estimated based on the poses $P_5$ and $P_8$, or based on the poses $P_6$, $P_7$ and $P_8$.

Various techniques of determining a registration between the patient 16 and patient image data comprising at least one image of the patient's body including the anatomical feature 20 exist. For instance, a probe tracked by the surgical tracking system 300 may be placed on (e.g., the anatomical feature 20 of) the patient 16 to obtain the first pose of (e.g., the anatomical feature 20 of) the patient 16 in the coordinate system $C_{tracking\ system}$. The first pose may then be correlated with or mapped to the patient image data to determine the registration between (e.g., the anatomical feature 20 of) the patient 16 and the patient image data. A relative pose $P_4$ between the coordinate system $C_{patient\ image\ data}$ of the patient image data and the coordinate system $C_{tracking\ system}$ of the surgical tracking system 300 may then be determined (e.g., based on the registration).

The content to be displayed to the surgeon 28 may be part of the patient image data or defined (e.g., planned) in the coordinate system $C_{patient\ image\ data}$. Based on the third pose $P_{10}$, the viewing direction 30 of the surgeon 28 onto (e.g., the anatomical feature 10 of) the patient 16 can be determined. The visualization may then be determined such that the content to be displayed is arranged in a similar orientation relative to the surgeon 28 like the patient 16 relative to the surgeon 28. In other words, the visualization of the content may be determined such that it corresponds or complies with a view of the surgeon 28 onto the patient 16.

As will become apparent from the above, the technique disclosed herein may provide numerous advantages. For example, the technique may allow for using a tracked portable display device that may be arranged very close to a surgical field. The portable display device may be a mobile tablet device. Contents such as surgical navigation information may be provided in close proximity to the surgical field. Compared with a HMD, the display of the portable display device may not block the surgeon's view. The display of the portable display device may not need to be arranged in a completely different viewing direction (e.g., on a cart), but may be arranged close to the surgical field. The surgeon may not need to adjust the focus of his eyes when shifting his field of view from the surgical field on the patient to the display or vice versa.

By tracking the positioning and orientation of the portable display device, a spatial relationship (e.g., the third pose) between the surgeon and the patient may be estimated. This information may be used to reduce the mental load for the surgeon.

The displayed content may be adjusted based on the pose of the surgeon relative to the portable display device. In particular, (e.g., navigated) content may be adjusted by rotating a screen perspective to comply with a real perspective of the surgeon. The surgeon may not need to mentally rotate the displayed information (e.g., the content and the one or more anatomical features or the representation thereof) when shifting his field of view from the surgical field to the display or vice versa.

The surgeon may not need to wear a tracker. His viewing direction may still be simulated on the display using the technique described herein. The surgeon may not need to wear a HMD to be provided with the displayed content.

The portable display device may be made sterile (e.g., via a surgical drape or other techniques) and may be used as a remote control through its touch screen capabilities. A gesture command may be detected by the portable display device as user input.

Based on the pose of the surgeon in relation to other tracked devices (e.g., surgical instruments), additional predefined actions may be performed (e.g., activating a workflow in a navigation software or adjusting the visualization).

Additional advantages may be apparent to those skilled in the art in view of the above. Various modifications to the technique disclosed herein are possible. For example, the first pose data may be obtained from a first tracking system and the second pose data may be obtained from a separate second tracking system (e.g., using a different tracking modality than the first tracking system). In another example, the second pose data may be obtained from the portable display device in case the portable display device is configured to determined its spatial pose relative on its own (e.g., using the sensor(s) comprised in the portable display device).

The invention claimed is:

1. A computer-implemented method for determining a visualization of content to be displayed to a surgeon on a display of a portable display device, the method comprising:

obtaining, from a surgical tracking system that is configured to track an anatomical feature or one or more trackers fixedly attached relative to the anatomical feature, first pose data indicative of a first pose of the anatomical feature of a patient in an operating room;

obtaining, from the surgical tracking system that is additionally configured to track the portable display device or one or more trackers fixedly attached relative to the portable display device, second pose data indicative of a second pose of the portable display device in the operating room;

obtaining a fourth pose of the surgeon relative to the portable display device, wherein the fourth pose is determined based on a predefined spatial criterion associated with the portable display device and additionally based on sensor data acquired by a sensor of the portable display device;

estimating, using a processor, based on the first pose data, the second pose data, and the fourth pose, a third pose of the surgeon relative to the patient, wherein the third pose is estimated without further tracking the surgeon using one or more trackers attached to the surgeon;

determining, using the processor, based on the estimated third pose, the visualization of the content to be displayed to the surgeon on a display of the portable display device; and triggering display of the visualization of the content on the display of the portable display device such that a projection of the visualization of the content along a line of sight of the surgeon complies with a view along a viewing direction of the surgeon onto the patient.

2. The computer-implemented method of claim 1, wherein the predefined spatial criterion defines that the fourth pose lies on a trajectory having a predefined spatial relationship relative to the portable display device.

3. The computer-implemented method of claim 1, wherein an approximate fourth pose is determined based on the predefined spatial criterion, and the approximate fourth pose is refined based on the sensor data to determine the fourth pose.

4. The computer-implemented method of claim 3, wherein the approximate fourth pose is refined based on the sensor data acquired by a camera or a depth sensor of the portable display device.

5. The computer-implemented method of claim 1, wherein the sensor comprises a camera and the sensor data comprises image data acquired by the camera.

6. The computer-implemented method of claim 5, wherein the camera of the portable display device is configured to acquire an image of the surgeon looking at the display of the portable display device.

7. The computer-implemented method of claim 1, wherein the visualization of the content is determined based on the viewing direction of the surgeon onto the patient.

8. The computer-implemented method of claim 7, wherein the visualization of the content is associated with one or more anatomical features of the patient having a predefined spatial relationship to the viewing direction.

9. The computer-implemented method of claim 8, wherein the visualization of the content is an augmented view of (i) the visualization of the content and (ii) the one or more anatomical features or a representation thereof.

10. The computer-implemented method of claim 9, wherein the visualization corresponds to the view of the surgeon onto the patient and comprises the content overlaid onto the view, wherein an orientation of the displayed content corresponds to the viewing direction of the surgeon onto the patient.

11. The computer-implemented method of claim 9, wherein the augmented view comprises the visualization of the content and a representation of the associated anatomical features selected from an image, model, or segmentation.

12. The computer-implemented method of claim 1, wherein the visualization of the content mimics the view of the surgeon onto the patient.

13. The computer-implemented method of claim 1, wherein the visualization of the content is adjusted based on the fourth pose of the surgeon relative to the portable display device.

14. The computer-implemented method of claim 1, further comprising:

comparing at least one pose selected from the second pose, the third pose and the fourth pose with a first criterion; and based on a result of the comparing, performing one or more predefined actions associated with the result.

15. The computer-implemented method of claim 1, further comprising:

obtaining user input entered via the portable display device; and performing one or more actions based on the obtained user input.

16. The computer-implemented method of claim 1, further comprising:

obtaining user input entered via the portable display device; and performing one or more actions based on the obtained user input, wherein the obtained user input comprises a gesture command entered via the sensor.

17. A system for determining a visualization of content to be displayed to a surgeon on a display of a portable display device, the system comprising:

the portable display device comprising a sensor;

a surgical tracking system configured to track an anatomical feature or one or more trackers fixedly attached relative to the anatomical feature and that is additionally configured to track the portable display device or one or more trackers fixedly attached relative to the portable display device; and at least one processor configured to:

obtain, from the surgical tracking system, first pose data indicative of a first pose of an anatomical feature of a patient in an operating room;

obtain, from the surgical tracking system, second pose data indicative of a second pose of the portable display device in the operating room;

obtain a fourth pose of the surgeon relative to the portable display device, wherein the fourth pose is determined based on a predefined spatial criterion associated with the portable display device, and additionally based on sensor data acquired by the sensor of the portable display device;

estimate, using the at least one processor, based on the first pose data, the second pose data, and the fourth pose, a third pose of the surgeon relative to the patient, wherein the third pose is estimated without further tracking the surgeon using one or more trackers attached to the surgeon;

determine, using the at least one processor, based on the estimated third pose, the visualization of the content to be displayed to the surgeon on the display of the portable display device; and trigger display of the visualization of the content on the display of the portable display device such that a projection of the visualization of the content along a line of sight complies with a view along a viewing direction of the surgeon onto the patient.

18. The system of claim 17, further comprising:

the surgical tracking system configured to track at least one entity selected from (i) the anatomical feature, (ii) the one or more trackers fixedly attached relative to the anatomical feature, (iii) the portable display device, and (iv) the one or more trackers fixedly attached relative to the portable display device, wherein the surgical tracking system is configured to provide the at least one processor with at least one input selected from the first pose data and the second pose data.

19. A non-transitory computer readable medium storing a computer program comprising instructions which, when executed on at least one processor, cause the at least one processor to:

obtain, from a surgical tracking system that is configured to track the anatomical feature or one or more trackers fixedly attached relative to the anatomical feature, first pose data indicative of a first pose of an anatomical feature of a patient in an operating room;

obtain, from the surgical tracking system that is additionally configured to track a portable display device or one or more trackers fixedly attached relative to the portable display device, second pose data indicative of a second pose of the portable display device in the operating room;

obtain a fourth pose of a surgeon relative to the portable display device, wherein the fourth pose is determined based on a predefined spatial criterion associated with the portable display device and additionally based on sensor data acquired by a sensor of the portable display device;

estimate, using the processor, based on the first pose data, the second pose data, and the fourth pose, a third pose of the surgeon relative to the patient, wherein the third pose is estimated without further tracking the surgeon using one or more trackers attached to the surgeon;

determine, using the processor, based on the estimated third pose, a visualization of content to be displayed to the surgeon on a display of the portable display device; and trigger display of the visualization of the content on the display of the portable display device such that a projection of the visualization of the content along a line of sight complies with a view along a viewing direction of the surgeon onto the patient.

\* \* \* \* \*